United States Patent [19]

Imuta et al.

[11] Patent Number: 5,616,663
[45] Date of Patent: Apr. 1, 1997

[54] TRANSITION METAL COMPOUND, OLEFIN POLYMERIZATION CATALYST COMPONENT COMPRISING THE TRANSITION METAL COMPOUND, OLEFIN POLYMERIZATION CATALYST COMPRISING THE OLEFIN POLYMERIZATION CATALYST COMPONENT, AND PROCESS FOR OLEFIN POLYMERIZATION

[75] Inventors: Junichi Imuta; Daisuke Fukuoka; Masayasu Yoshida; Junji Saito; Terunori Fujita; Takashi Tashiro; Koji Kawaai; Takashi Ueda; Yoshihisa Kiso, all of Waki-cho, Japan

[73] Assignee: Mitsui Petrochemical Industries, Ltd., Tokyo, Japan

[21] Appl. No.: 338,810

[22] Filed: Nov. 10, 1994

[30] Foreign Application Priority Data

Nov. 12, 1993 [JP] Japan ..................... 5-283778

[51] Int. Cl.⁶ ..................... C08F 4/60; C08F 4/622; C08F 10/00
[52] U.S. Cl. ..................... 526/127; 502/103; 502/153; 526/113; 526/114; 526/115; 526/129; 526/131; 526/133; 526/153; 526/160; 526/150; 526/152; 526/126; 526/351
[58] Field of Search ..................... 526/127, 126, 526/152, 150, 153, 160

[56] References Cited

U.S. PATENT DOCUMENTS

| | | | |
|---|---|---|---|
| 5,278,264 | 1/1994 | Spaleck et al. | 526/160 |
| 5,308,816 | 5/1994 | Tsutsui et al. | 526/129 |
| 5,328,969 | 7/1994 | Winter et al. | 526/127 |

FOREIGN PATENT DOCUMENTS

| | | |
|---|---|---|
| 2055219 | 5/1992 | Canada . |
| 2084017 | 5/1993 | Canada . |
| 0485823 | 5/1992 | European Pat. Off. . |
| 0549900 | 7/1993 | European Pat. Off. . |

*Primary Examiner*—Edward J. Smith
*Attorney, Agent, or Firm*—Sherman and Shalloway

[57] ABSTRACT

Disclosed is a novel transition metal compound represented by the following formula:

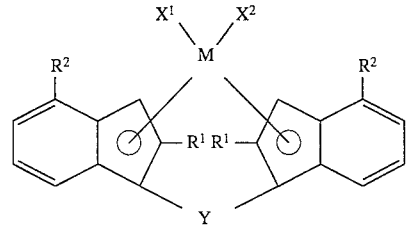

wherein M is a transition metal, X is halogen or the like, $R^1$ is a hydrocarbon group or the like, $R^2$ is an aryl group substituted with a halogenated hydrocarbon group, and Y is a divalent silicon-containing group or the like.

Also disclosed are an olefin polymerization catalyst component comprising the transition metal compound, an olefin polymerization catalyst comprising the olefin polymerization catalyst component, and a process for olefin polymerization using the olefin polymerization catalyst.

An olefin polymerization catalyst component having high polymerization activity can be formed from the transition metal compound. By the use of the olefin polymerization catalyst or the process for olefin polymerization, polyolefins having a high melting point and a high molecular weight can be prepared with high polymerization activity.

22 Claims, 1 Drawing Sheet

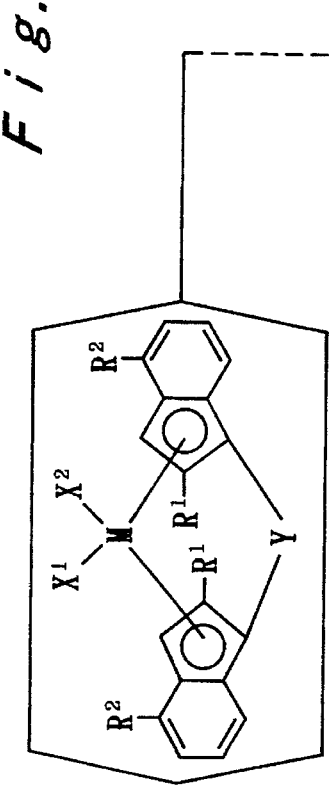

TRANSITION METAL COMPOUND, OLEFIN POLYMERIZATION CATALYST COMPONENT COMPRISING THE TRANSITION METAL COMPOUND, OLEFIN POLYMERIZATION CATALYST COMPRISING THE OLEFIN POLYMERIZATION CATALYST COMPONENT, AND PROCESS FOR OLEFIN POLYMERIZATION

FIELD OF THE INVENTION

The present invention relates to a novel transition metal compound, an olefin polymerization catalyst component comprising the transition metal compound, an olefin polymerization catalyst containing the olefin polymerization catalyst component and a process for olefin polymerization using the olefin polymerization catalyst.

BACKGROUND OF THE INVENTION

The "Kaminsky catalyst" is well known as a homogeneous catalyst system for olefin polymerization. This catalyst has an extremely high polymerization activity, and provides a polymer having a narrow molecular weight distribution.

Of the transition metal compounds used for the Kaminsky catalyst, for example, ethylenebis(indenyl)zirconium dichloride and ethylenebis(4,5,6,7-tetrahydroindenyl)zirconium dichloride has been known to be used for producing isotactic polyolefins, as described in Japanese Patent Laid-Open Publication No. 130314/1986. However, polyolefins prepared by the use of such catalyst generally have a low stereoregularity and a low molecular weight. If low temperatures are used, polymers having a high stereoregularity or a high molecular weight can be obtained, but a problem of low polymerization activity is involved.

It has been known that use of hafnium compounds in place of the zirconium compounds makes it possible to prepare high molecular polymers, as described in Journal of Molecular Catalysis, 56 (1989), pp. 237–247, but this process involves a problem of low polymerization activity. Further, compounds such as dimethylsilylbis-substituted cyclopentadienylzirconium dichloride have also been known from Japanese Patent Laid-Open Publication No. 130704/1989 and Polymer Preprints, Japan, vol. 39, No. 6, pp. 1,614–1616 (1990), but there is a problem in that they do not satisfy all of the high polymerization activity, and the high melting point and molecular weight at the same time.

Japanese Patent Laid-Open Publication No. 268307/1992 describes an olefin polymerization catalyst formed from a metallocene compound represented by the following formula

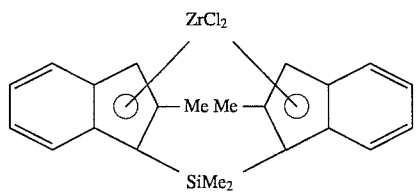

and an aluminoxane.

Further, EP 0 530 648 A1 describes another olefin polymerization catalyst formed from a metallocene compound represented by the following formula

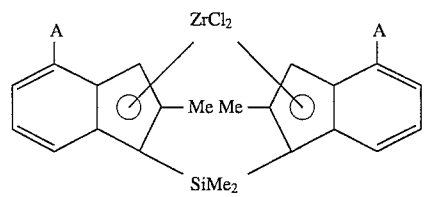

wherein A is a lower alkyl group, and an aluminoxane.

However, the polyolefins obtained by the use of these catalysts are still insufficient in the melting point, the molecular weight, etc. In this connection, a catalyst containing a compound of the above formula wherein A is a phenyl group is disclosed by Hoechst AG. in 40 YEARS ZIEGLER CATALYSIS IN HONOR OF KARL ZIEGLER AND WORKSHOP (Sep. 1–3, 1993). However, there remains a problem that the polyolefins obtained by the use of this catalyst still have a low melting point and a low molecular weight.

Under these circumstances, the advent of an olefin polymerization catalyst and a process for olefin polymerization, each of which shows a high olefin polymerization activity and produces polyolefins of excellent properties, is desired. Further, also desired is the advent of a catalyst component which can be used for such olefin polymerization catalyst and a novel transition metal compound which can be used as the olefin polymerization catalyst component.

OBJECT OF THE INVENTION

It is an object of the present invention to provide a novel transition metal compound which can be used as an olefin polymerization catalyst component showing a high olefin polymerization activity and to provide an olefin polymerization catalyst component comprising the transition metal compound. It is another object of the invention to provide an olefin polymerization catalyst comprising the olefin polymerization catalyst component and to provide a process for olefin polymerization using the olefin polymerization catalyst.

SUMMARY OF THE INVENTION

The novel transition metal compound according to the invention is a transition metal compound represented by the following formula [I]:

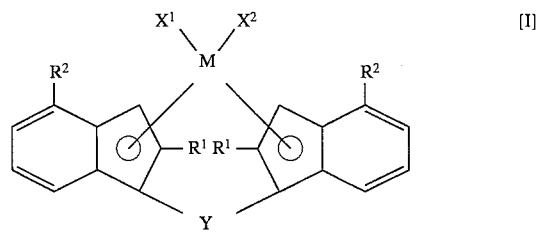

wherein M is a transition metal of Group IVa, Va or VIa of the periodic table, each $R^1$ is a hydrocarbon group of 1 to 20 carbon atoms, each $R^2$ is an aryl group of 6 to 16 carbon atoms substituted with a halogenated hydrocarbon group of 1 to 20 carbon atoms, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$—, where R$^3$ is a hydrogen atom, a halogen atom, a hydrocarbon group of 1 to 20 carbon atoms or a halogenated hydrocarbon group of 1 to 20 carbon atoms.

The olefin polymerization catalyst component according to the invention comprises a transition metal compound represented by the above formula [I].

The first olefin polymerization catalyst according to the invention comprises:

(A) a transition metal compound represented by the above formula [I]; and (B) at least one compound selected from the group consisting of:
(B-1) an organoaluminum oxy-compound, and
(B-2) a compound which reacts with the transition metal compound (A) to form an ion pair.

The second olefin polymerization catalyst according to the invention comprises:

(A) a transition metal compound represented by the above formula [I];

(B) at least one compound selected from the group consisting of (B-1) and (B-2) as defined above; and (C) an organoaluminum compound.

The third olefin polymerization catalyst according to the invention comprises:

a fine particle carrier;
(A) a transition metal compound represented by the above formula [I]; and
(B) at least one compound selected from the group consisting of (B-1) and (B-2) as defined above;

said transition metal compound (A) and said at least one compound (B) being supported on the fine particle carrier.

The fourth olefin polymerization catalyst according to the invention comprises:

a solid catalyst component which comprises:
a fine particle carrier;
(A) a transition metal compound represented by the above formula [I]; and
(B) at least one compound selected from the group consisting of (B-1) and (B-2) as defined above;
said transition metal compound (A) and said at least one compound (B) being supported on the fine particle carrier; and
(C) an organoaluminum compound.

The fifth olefin polymerization catalyst according to the invention comprises:

a fine particle carrier;
(A) a transition metal compound represented by the above formula [I];
(B) at least one compound selected from the group consisting of (B-1) and (B-2) as defined above; and
an olefin polymer produced by prepolymerization.

The sixth olefin polymerization catalyst according to the invention comprises:

a fine particle carrier;
(A) a transition metal compound represented by the above formula [I];
(B) at least one compound selected from the group consisting of (B-1) and (B-2) as defined above;

(C) an organoaluminum compound; and
an olefin polymer produced by prepolymerization.

The process for olefin polymerization according to the invention comprises polymerizing or copolymerizing an olefin in the presence of any one of the first to sixth olefin polymerization catalysts or in the presence of the fifth or the sixth olefin polymerization catalyst and an organoaluminum compound.

BRIEF DESCRIPTION OF THE DRAWING

FIG. 1 is an explanatory view showing steps of a process for preparing an olefin polymerization catalyst according to the invention.

DETAILED DESCRIPTION OF THE INVENTION

The novel transition metal compound, the olefin polymerization catalyst component comprising the transition metal compound, the olefin polymerization catalyst comprising the olefin polymerization catalyst component and the process for olefin polymerization using the olefin polymerization catalyst, according to the invention, will be described in detail hereinafter.

First, the novel transition metal compound according to the invention is explained.

The novel transition metal compound according to the invention is a transition metal compound represented by the following formula [I].

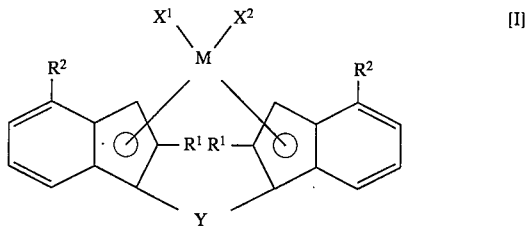

In this formula, M is a transition metal of Group IVa, Va or VIa of the periodic table. Examples of the transition metals include titanium, zirconium, hafnium, vanadium, niobium, tantalum, chromium, molybdenum and tungsten. Of these, titanium, zirconium and hafnium are preferred, and zirconium is particularly preferred.

Each R$^1$ is a hydrocarbon group of 1 to 20 carbon atoms, including, for example, an alkyl group such as methyl, ethyl, propyl, butyl, hexyl, cyclohexyl, methylcyclohexyl, octyl, nonyl, dodecyl, icosyl, norbornyl and adamantyl; an alkenyl group such as vinyl, propenyl and cyclohexenyl; an arylalkyl group such as benzyl, phenylethyl and phenylpropyl; and an aryl group such as phenyl, tolyl, dimethylphenyl, trimethylphenyl, ethylphenyl, propylphenyl, biphenyl, naphthyl, methylnaphthyl, anthracenyl and phenanthryl.

Of these, particularly preferred are alkyl groups of 1 to 4 carbon atoms such as methyl, ethyl, propyl and butyl.

The groups R$^1$ may be the same or different from each other.

Each R$^2$ is an aryl group of 6 to 16 carbon atoms substituted with a halogenated hydrocarbon group of 1 to 20 carbon atoms.

Examples of the aryl groups of 6 to 16 carbon atoms include phenyl, α-naphthyl, β-naphthyl, anthryl, phenanthryl, pyrenyl, acenaphthyl, phenalenyl and aceanthryl. Of these, preferred are phenyl and naphthyl.

These aryl groups are substituted with a halogenated hydrocarbon group wherein the above-mentioned hydrocarbon group of 1 to 20 carbon atoms has one or more halogen atoms such as F, Cl, Br and I as a substituent.

Examples of the halogenated hydrocarbon groups include fluoromethyl, difluoromethyl, trifluoromethyl, chloromethyl, dichloromethyl, trichloromethyl, bromomethyl, dibromomethyl, tribromomethyl, iodomethyl, 2,2,2-trifluoroethyl, 2,2,1,1-tetrafluoroethyl, pentafluoroethyl, pentachloroethyl, heptafluoropropyl, nonafluorobutyl, tirfluorovinyl, 1,1-difluorobenzyl, 1,1,2,2-tetrafluorophenylethyl, pentafluorophenyl, pentachlorophenyl, heptafluoro-α-naphthyl, heptafluoro-β-naphthyl and 4-trifluoromethyl-β-naphthyl. Of these, preferred are fluorinated hydrocarbon groups, and particularly preferred are fluorinated alkyl groups of 1 to 3 carbon atoms.

Examples of the aryl groups of 6 to 16 carbon atoms substituted with halogenated hydrocarbon groups of 1 to 20 carbon atoms include o-, m- or p-trifluoromethylphenyl, o-, m- or p-trichloromethylphenyl, 2,4-di-trifluoromethylphenyl, 3,5-, 2,6- or 2,5-ditrifluoromethylphenyl, 2,4,6-tri-trifluoromethylphenyl, 4-trifluoromethylnaphthyl, 4-trichloromethylnaphthyl and 2,4-di-trifluoromethylnaphthyl. Of these, preferred are o-, m- or p-trifluoromethylphenyl and 2,4- or 3,5-ditrifluoromethylphenyl.

The groups $R^2$ may be the same or different from each other.

$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and examples thereof include:

halogen atoms such as fluorine, chlorine, bromine and iodine;

hydrocarbon groups of 1 to 20 carbon atoms such as those as described for $R^1$;

halogenated hydrocarbon groups of 1 to 20 carbon atoms such as those as described for $R^2$; and oxygen-containing groups such as a hydroxyl group, an alkoxy group (e.g., methoxy, ethoxy, propoxy, butoxy), aryloxy group (e.g., phenoxy, methylphenoxy, dimethylphenoxy, naphthoxy) and an arylalkoxy group (e.g., phenylmethoxy, phenylethoxy).

Examples of the sulfur-containing groups include substituents corresponding to the above-mentioned oxygen-containing groups wherein oxygen is replaced by sulfur; and further sulfonato groups such as methylsulfonato, trifluoromethanesulfonato, phenylsulfonato, benzylsulfonate, p-toluenesulfonato, trimethylbenzenesulfonato, triisobutylbenzenesulfonate, p-chlorobenzenesulfonato and pentafluorobenzenesulfonate; and sulfinato groups such as methylsulfinato, phenylsulfonato, benzylsulfinato, p-toluenesulfinato, trimethylbenzenesulfinato and pentafluorobenzenesulfinato.

Of these, preferred are halogen atoms and hydrocarbon groups of 1 to 20 carbon atoms.

Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$— where R$^3$ is a hydrogen atom, a halogen atom, a hydrocarbon group of 1 to 20 carbon atoms or a halogenated hydrocarbon group of 1 to 20 carbon atoms; and examples of these groups include:

divalent hydrocarbon groups of 1 to 20 carbon atoms such as an alkylene group (e.g., methylene, dimethylmethylene, 1,2-ethylene, dimethyl-1,2-ethylene, 1,3-trimethylene, 1,4-tetramethylene, 1,2-cyclohexylene, 1,4-cyclohexylene) and an arylalkylene group (e.g., diphenylmethylene, diphenyl-1,2-ethylene);

divalent halogenated hydrocarbon groups wherein the above-mentioned divalent hydrocarbon groups of 1 to 20 carbon atoms are substituted with one or more halogen atoms, such as chloromethylene;

divalent silicon-containing groups such as alkylsilylene, alkylarylsilylene and arylsilylene groups (e.g., methylsilylene, dimethylsilylene, diethylsilylene, di(n-propyl)silylene, di(i-propyl)silylene, di(cyclohexyl)silylene, methylphenylsilylene, diphenylsilylene, di(p-tolyl)silylene, di(p-chlorophenyl)silylene), and alkyldisilyl, alkylaryldisilyl and aryldisilyl groups (e.g., tetramethyl-1,2-disilyl, tetraphenyl-1,2-disilyl);

divalent germanium-containing groups corresponding to the above-mentioned divalent silicon-containing groups wherein silicon is replaced by germanium; and divalent tin-containing groups corresponding to the above-mentioned silicon-containing groups wherein silicon is replaced by tin.

$R^3$ is a hydrogen atom, a halogen atom, a hydrocarbon group of 1 to 20 carbon atoms or a halogenated hydrocarbon group of 1 to 20 carbon atoms, and these halogen atom, hydrocarbon group of 1 to 20 carbon atoms and halogenated hydrocarbon group of 1 to 20 carbon atoms may be those described above, respectively.

Of these, preferred as $R^3$ are divalent silicon-containing groups, divalent germanium-containing groups and divalent tin-containing groups. Among them, more preferred are silicon-containing groups, and particularly preferred are alkylsilylene, alkylarylsilylene and arylsilylene.

Listed below are examples of the transition metal compounds represented by the above formula [I].

rac-Dimethylsilylene-bis(2-methyl-4-(p-trifluoromethylphenyl)-1-indenyl)zirconium dichloride, rac-Dimethylsilylene-bis(2-methyl-4-(m-trifluoromethylphenyl)-1-indenyl)zirconium dichloride, rac-Dimethylsilylene-bis(2-methyl-4-(o-trifluoromethylphenyl)-1-indenyl)zirconium dichloride, rac-Dimethylsilylene-bis(2-ethyl-4-(p-trifluoromethylphenyl)-1-indenyl)zirconium dichloride, rac-Dimethylsilylene-bis(2-n-propyl-4-(p-trifluoromethylphenyl)-1-indenyl)zirconium dichloride, rac-Dimethylsilylene-bis(2-n-butyl-4-(p-trifluoromethylphenyl)-1-indenyl)zirconium dichloride, rac-Dimethylsilylene-bis(2-i-butyl-4-(p-trifluoromethylphenyl)-1-indenynl)zirconium dichloride, rac-Dimethylsilylene-bis(2-methyl-4-(2,4-di-trifluoromethylphenyl)-1-indenyl)zirconium dichloride, rac-Dimethylsilylene-bis(2-ethyl-4-(2,4-di-trifluoromethylphenyl)-1-indenyl)zirconium dichloride, rac-Dimethylsilylene-bis(2-methyl-4-(3,5-di-trifluoromethylphenyl)-1-indenyl)zirconium dichloride, rac-Dimethylsilylene-bis(2-ethyl-4-(3,5-di-trifluoromethylphenyl)-1-indenyl)zirconium dichloride, rac-Dimethylsilylene-bis(2-methyl-4-(2,4,6-tri-trifluoromethylphenyl)-1-indenyl)zirconium dichloride, rac-Dimethylsilylene-bis(2-ethyl-4-(2,4,6-tri-trifluoromethylphenyl)-1-indenyl)zirconium dichloride, rac-Dimethylsilylene-bis(2-ethyl-4-(p-pentafluoroethylphenyl)-1-indenyl)zirconium dichloride, rac-Dimethylsilylene-bis(2-methyl-4-(4-trifluoromethyl-α-naphthyl)-1-indenyl)zirconium dichloride, rac-Dimethylsilylene-bis(2-ethyl-4-(2,4-di-trifluoromethyl-
(α-naphthyl)-1-indenyl)zirconium dichloride,
rac-Phenylmethylsilylene-bis(2-ethyl-4-(p-trifluoromethylphenyl)-1-indenyl)zirconium dichloride,
rac-Diphenylsilylene-bis(2-ethyl-4-(p-trifluoromethylphenyl)-1-indenyl)zirconium dichloride,
rac-Methylene-bis(2-ethyl-4-(p-trifluoromethylphenyl)-1-indenyl)zirconium dichloride,
rac-Ethylene-bis(2-ethyl-4-(p-trifluoromethylphenyl)-1-indenyl)zirconium dichloride,
rac-Ethylene-bis(2-n-propyl-4-(p-trifluoromethylphenyl)-1-indenyl)zirconium dichloride,
rac-Dimethylgermylene-bis(2-ethyl-4-(p-trifluoromethylphenyl)-1-indenyl)zirconium dichloride,
rac-Dimethylgermylene-bis(2-n-propyl-4-(p-trifluoromethylphenyl)-1-indenyl)zirconium dichloride,
rac-Dimethylstannylene-bis(2-ethyl-4-(p-trifluoromethylphenyl)-1-indenyl)zirconium dichloride,
rac-Dimethylstannylene-bis(2-ethyl-4-(4-trifluoromethyl-α-naphthyl)-1-indenyl)zirconium dichloride,
rac-Dimethylstannylene-bis(2-n-propyl-4-(p-trifluoromethylphenyl)-1-indenyl)zirconium dichloride,
rac-Dimethylsilylene-bis(2-methyl-4-(p-trifluoromethylphenyl)-1-indenyl)zirconium dimethyl,
rac-Dimethylsilylene-bis(2-methyl-4-(p-trifluoromethylphenyl)-1-indenyl)zirconium methylchloride,
rac-Dimethylsilylene-bis(2-methyl-4-(p-trifluoromethylphenyl)-1-indenyl)zirconium chloride $SO_2Me$,
rac-Dimethylsilylene-bis(2-methyl-4-(p-trifluoromethylphenyl)-1-indenyl)zirconium chloride $OSO_2Me$,
rac-Dimethylsilylene-bis(2-methyl-4-(p-trifluoromethylphenyl)-1-indenyl)titanium dichloride, and
rac-Dimethylsilylene-bis(2-methyl-4-(p-trifluoromethylphenyl)-1-indenyl)hafnium dichloride.

In the present invention, transition metal compounds corresponding to the above zirconium compound wherein zirconium is replaced by titanium, hafnium, vanadium, niobium, tantalum, chromium, molybdenum or tungsten, can be also employed.

These novel transition metal compounds of the invention can be prepared, for example, in accordance with Journal of Organometallic Chem. 288 (1985), pp. 64–77, and European Patent Laid-Open Publication No. 0,320,762, as follows:

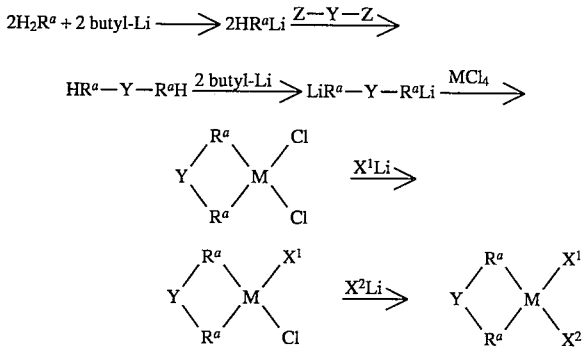

wherein Z is Cl, Br, I or o-tosyl group, and $H_2R^a$ is

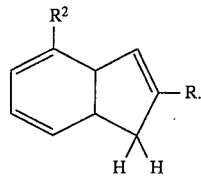

The novel transition metal compound of the invention can be used as an olefin polymerization catalyst component in combination with an organoaluminum oxy-compound, etc.

The transition metal compound is used in an olefin polymerization catalyst in the form of usually a racemic modification, but it can be also used in the form of R configuration or S configuration.

Next, the olefin polymerization catalyst containing the above-mentioned novel transition metal compound as its catalyst component is described. FIG. 1 shows steps of a process for preparing an olefin polymerization catalyst of the invention.

The meaning of the term "polymerization" used herein is not limited to "homopolymerization" but may comprehend "copolymerization". Also, the meaning of the term "polymer" used herein is not limited to "homopolymer" but may comprehend "copolymer".

The first and the second olefin polymerization catalysts according to the invention are now explained.

The first olefin polymerization catalyst of the invention is formed from:

(A) a transition metal compound represented by the above formula [I] (hereinafter sometimes referred to as "component (A)"); and (B) at least one compound selected from the group consisting of:
   (B-1) an organoaluminum oxy-compound, and
   (B-2) a compound which reacts with the transition metal compound (A) to form an ion pair.

The second olefin polymerization catalyst of the invention is formed from:

(A) a transition metal compound represented by the above formula [I];

(B) at least one compound selected from the group consisting of (B-1) and (B-2) as defined above; and (C) an organoaluminum compound.

The organoaluminum oxy-compound (B-1) (hereinafter sometimes referred to as "component (B-1)") used for the first and the second olefin polymerization catalysts of the invention may be a conventionally known aluminoxane or may be such a benzene-insoluble organoaluminum oxy-compound as described in Japanese Patent Laid-Open Publication No. 78687/1990.

The conventionally known aluminoxane can be prepared, for example, by the following procedures.

(1) A procedure of adding an organoaluminum compound such as trialkylaluminum to a hydrocarbon medium suspension of compounds containing adsorbed water or salts containing water of crystallization, e.g., magnesium chloride hydrate, copper sulfate hydrate, aluminum sulfate hydrate, nickel sulfate hydrate and cerous chloride hydrate, so as to allow them to react with each other.

(2) A procedure of allowing water, ice or water vapor to directly act on an organoaluminum compound such as trialkylaluminum in a medium such as benzene, toluene, ethyl ether or tetrahydrofuran.

(3) A procedure of causing organotin oxide such as dimethyltin oxide or dibutyltin oxide to react with an organoaluminum compound such as trialkylaluminum in a medium such as decane, benzene or toluene.

The aluminoxane may contain a small amount of an organometallic component. Moreover, it is possible that the solvent or the unreacted organoaluminum compound is distilled off from the aluminoxane solution recovered and the residue is dissolved again in a solvent.

Examples of the organoaluminum compounds for use in the preparation of aluminoxane include:

trialkylaluminums, such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, trihexylaluminum, trioctylaluminum and tridecylaluminum;

tricycloalkylaluminums, such as tricyclohexylaluminum and tricyclooctylaluminum;

dialkylaluminum halides, such as dimethylaluminum chloride, diethylaluminum chloride, diethylaluminum bromide and diisobutylaluminum chloride;

dialkylaluminum hydrides, such as diethylalumimum hydride and diisobutylaluminum hydride;

dialkylaluminum alkoxides, such as diethylaluminum methoxide and diethylaluminum ethoxide; and dialkylaluminum aryloxides, such as diethylaluminum phenoxide.

Of these, trialkylaluminums and tricycloalkylaluminums are particularly preferred.

Also employable as the organoaluminum compound used for preparing aluminoxane is isoprenylaluminum represented by the following formula [II]:

$$(i-C_4H_9)_xAl_y(C_5H_{10})_z \qquad [II]$$

wherein x, y and z are each a positive number, and $z \geq 2x$.

The organoaluminum compounds mentioned above may be used singly or in combination.

Examples of the solvents used in the aluminoxane solution include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosene and gas oil; and halides of the aromatic, aliphatic and alicyclic hydrocarbons, particularly chlorides and bromides thereof. In addition, ethers such as ethyl ether and tetrahydrofuran can be also employed. Of these solvents, aromatic hydrocarbons are particularly preferred.

The compound (B-2) which reacts with the transition metal compound (A) to form an ion pair (hereinafter sometimes referred to as "component (B-2)"), that is used for the first and the second olefin polymerization catalysts of the invention, includes Lewis acid, ionic compounds, borane compounds and carborane compounds, as described in National Publications of International Patent No. 501950/1989 and No. 502036/1989, Japanese Patent Laid-Open Publications No. 179005/1991, No. 179006/1991, No. 207703/1991 and No. 207704/1991, and U.S. Pat. No. 547,718.

The Lewis acid includes Mg-containing Lewis acid, Al-containing Lewis acid and B-containing Lewis acid. Of these, B-containing Lewis acid is preferred.

The Lewis acid which contains a boron atom is, for example, a compound represented by the following formula:

$BR^4R^5R^6$ wherein $R^4$, $R^5$ and $R^6$ are each independently a phenyl group which may have a substituent such as a fluorine atom, a methyl group or a trifluoromethyl group, or a fluorine atom.

Examples of the compounds represented by the above formula include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethylphenyl)boron. Of these, particularly preferred is tris(pentafluorophenyl)boron.

The ionic compound employable in the invention is a salt comprising a cationic compound and an anionic compound. The anion reacts with the transition metal compound (A) to render the transition metal compound (A) cationic and to form an ion pair, resulting in stabilizing the transition metal cation species. Examples of such anion include organoboron compound anion, organoarsenic compound anion and organoaluminum compound anion. Preferred are those relatively bulky and stabilizing the transition metal cation species. Examples of cation include metallic cation, organometallic cation, carbonium cation, tripium cation, oxonium cation, sulfonium cation, phosphonium cation and ammonium cation. More specifically, there can be mentioned triphenylcarbenium cation, tributylammonium cation, N,N-dimethylammonium cation, ferrocenium cation, etc.

Of these, preferred are ionic compounds containing a boron compound as anion, and examples thereof include:

trialkyl-substituted ammonium salts, such as triethylammoniumtetra(phenyl)boron, tripropylammoniumtetra(phenyl)boron, tri(n-butyl)ammoniumtetra(phenyl)boron, trimethylammoniumtetra(p-tolyl)boron, trimethylammoniumtetra(o-tolyl)boron, tributylammoniumtetra(pentafluorophenyl)boron, tripropylammoniumtetra(o,p-dimethylphenyl)boron, tributylammoniumtetra(m,m-dimethylphenyl)boron, tributylammoniumtetra(p-trifluoromethylphenyl)boron, tri(n-butyl)ammoniumtetra(o-tolyl)boron and tri(n-butyl)ammoniumtetra(4-fluorophenyl)boron;

N,N-dialkylanilinium salts, such as N,N-dimethylaniliniumtetra(phenyl)boron, N,N-diethylaniliniumtetra(phenyl)boron and N,N-2,4,6-pentamethylaniliniumtetra(phenyl)boron;

dialkylammonium salts, such as di(n-propyl)ammoniumtetra(pentafluorophenyl)boron and dicyclohexylammoniumtetra(phenyl)boron; and triarylphosphonium salts, such as triphenylphosphoniumtetra(phenyl)boron, tri(methylphenyl)phosphoniumtetra(phenyl)boron and tri(dimethylphenyl)phosphoniumtetra(phenyl)boron.

Also employable as the ionic compound which contains a boron atom are triphenylcarbeniumtetrakis(pentafluorophenyl)borate, N,N-dimethylaniliniumtetrakis(pentafluorophenyl)borate and ferroceniumtetrakis(pentafluorophenyl)borate.

Further, the following compounds can be also employed. (In the ionic compounds enumerated below, the counter ion is tri(n-butyl)ammonium, but the counter ion is in no way limited thereto.)

Salts of anions, for example, bis{tri(n-butyl)ammonium}nonaborate, bis{tri(n-butyl)ammonium}decaborate, bis{tri(n-butyl)ammonium}undecaborate, bis{tri(n-butyl)ammonium}dodecaborate, bis{tri(n-butyl)ammonium}decachlorodecaborate, bis{tri(n-butyl)ammonium}dodecachlorododecaborate, tri(n-butyl)ammonium-1-carbadecaborate, tri(n- butyl)ammonium-1-carbaundecaborate, tri(n-butyl)ammonium-1-carbadodecaborate, tri(n-butyl)ammonium-1-trimethylsilyl-1-carbadecaborate and tri(n-butyl)ammonium-bromo-1-carbadodecaborate.

Moreover, borane compounds and carborane compounds can be also employed. These compounds are employed as the Lewis acids or the ionic compounds.

Examples of the borane and carborane compounds include:

borane and carborane complex compounds and salts of carborane anions, for example, decaborane(14), 7,8-dicarbaundecaborane(13), 2,7-dicarbaundecaborane(13), undecahydride-7,8-dimethyl-7,8-dicarbaundecaborane, dodecahydride-11-methyl-2,7-dicarbaundecaborane, tri(n-butyl)ammonium-6-carbadecaborate(14), tri(n-butyl)ammonium-6-carbadecaborate(12), tri(n-butyl)ammonium-7-carbaundecaborate (13), tri(n-butyl)ammonium-7,8-dicarbaundecaborate(12), tri(n-butyl)ammonium-2,9-dicarbaundecaborate(12), tri(n-butyl)ammoniumdodecahydride-8-methyl-7,9-dicarbaundecaborate, tri(n-butyl)ammoniumundecahydride-8-ethyl-7,9-dicarbaundecaborate, tri(n-butyl)ammoniumundecahydride-8-butyl-7,9-dicarbaundecaborate, tri(n-butyl)ammoniumundecahydride-8-allyl-7,9-dicarbaundecaborate, tri(n-butyl)ammoniumundecahydride-9-trimethylsilyl-7,8-dicarbaundecaborate and tri(n-butyl)ammoniumundecahydride-4,6-dibromo-7-carbaundecaborate; and carborane and salts of carborane, for example, 4-carbanonaborane (14), 1,3-dicarbanonaborane(13), 6,9-dicarbadecaborane(14), dodecahydride-1-phenyl-1,3-dicarbanonaborane, dodecahydride-1-methyl-1,3-dicarbanonaborane and undecahydride-1,3-dimethyl-1,3-dicarbanonaborane.

Furthermore, the following compounds can be also employed.(In the ionic compounds enumerated below, the counter ion is tri(n-butyl)ammonium, but the counter ion is in no way limited thereto.)

Salts of metallic carboranes and metallic borane anions, for example, tri(n-butyl)ammoniumbis(nonahydride-1,3-dicarbanonaborate)cobaltate(III), tri(n-butyl)ammoniumbis(undecahydride-7,8-dicarbaundecaborate)ferrate(III), tri(n-butyl)ammoniumbis(undecahydride-7,8dicarbaundecaborate)cobaltate(III), tri(n-butyl)ammoniumbis(undecahydride-7,8dicarbaundecaborate)nickelate(III), tri(n-butyl)ammoniumbis(undecahydride-7,8-dicarbaundecaborate)cuprate(III), tri(n-butyl)ammoniumbis(undecahydride-7,8-dicarbaundecaborate)aurate(III), tri(n-butyl)ammoniumbis(nonahydride-7,8-dimethyl-7,8-dicarbaundecaborate)ferrate(III), tri(n-butyl)ammoniumhis(nonahydride-7,8-dimethyl-7,8-dicarbaundecaborate)chromate(III), tri(n-butyl)ammoniumbis(tribromooctahydride-7,8dicarbaundecaborate)cobaltate(III), tri(n-butyl)ammoniumbis(dodecahydridedicarbadodecaborate)cobaltate(III), bis{tri(n-butyl)ammonium}bis(dodecahydridedodecaborate)nickelate(III), tris{tri(n-butyl)ammonium}bis(undecahydride-7-carbaundecaborate)chromate(III), bis{tri(n-butyl)ammonium}bis(undecahydride-7-carbaundecaborate) manganate(IV), bis{tri(n-butyl)ammonium}bis(undecahydride-7-carbaundecaborate) cobaltate(III) and bis{tri(n-butyl)ammonium}bis(undecahydride-7-carbaundecaborate) nickelate(IV).

The compound (B-2) which reacts with the transition metal compound (A) to form an ion pair can be used in combination of two or more kinds.

The organoaluminum compound (C) (hereinafter sometimes referred to as "component (C)") used for the second olefin polymerization catalyst of the invention is, for example, an organoaluminum compound represented by the following formula [III]:

$$R^7_n AlX_{3-n} \qquad [III]$$

wherein $R^7$ is a hydrocarbon group of 1 to 12 carbon atoms, X is a halogen atom or a hydrogen atom, and n is 1 to 3.

Examples of the hydrocarbon groups of 1 to 12 carbon atoms include an alkyl group, a cycloalkyl group and an aryl group, more specifically, methyl, ethyl, n-propyl, isopropyl, isobutyl, pentyl, hexyl, octyl, cyclopentyl, cyclohexyl, phenyl, tolyl, etc.

Examples of such organoaluminum compounds (C) include:

trialkylaluminums, such as trimethylaluminum, triethylaluminum, triisopropylaluminum, triisobutylaluminum, trioctylaluminum and tri(2-ethylhexyl)aluminum;

alkenylaluminums, such as isoprenylaluminum;

dialkylaluminum halides, such as dimethylaluminum chloride, diethylaluminum chloride, diisopropylaluminum chloride, diisobutylaluminum chloride and dimethylaluminum bromide;

alkylaluminum sesquihalides, such as methylaluminum sesquichloride, ethylaluminum sesquichloride, isopropylaluminum sesquichloride, butylaluminum sesquichloride and ethylaluminum sesquibromide;

alkylaluminum dihalides, such as methylaluminum dichloride, ethylaluminum dichloride, isopropylaluminum dichloride and ethylaluminum dibromide; and alkylaluminum hydrides, such as diethylaluminum hydride and diisobutylaluminum hydride.

Also employable as the organoaluminum compound (C) is a compound represented by the following formula [IV]:

$$R^7_n AlL_{3-n} \qquad [IV]$$

wherein $R^7$ is the hydrocarbon group as described above;

L is —$OR^8$ group, —$OSiR^9_3$ group, —$OAlR^{10}_2$ group, —$NR^{11}_2$ group, —$SiR^{12}_3$ group or —$N(R^{13})AlR^{14}_2$ group;

n is 1 or 2; $R^8$, $R^9$, $R^{10}$ and $R^{14}$ are each methyl, ethyl, isopropyl, isobutyl, cyclohexyl, phenyl or the like;

$R^{11}$ is hydrogen, methyl, ethyl, isopropyl, phenyl, trimethylsilyl or the like; and $R^{12}$ and $R^{13}$ are each methyl, ethyl or the like.

Examples of such organoaluminum compounds include:

(1) compounds of the formula $R^7_n Al(OR^8)_{3-n}$, for example, dimethylaluminum methoxide, diethylaluminum ethoxide and diisobutylaluminum methoxide;

(2) compounds of the formula $R^7_n Al(OSiR^9_3)$, for example, $Et_2Al(OSiMe_3)$, $(iso-Bu)_2Al(OSiMe_3)$ and $(iso-Bu)_2Al(OSiEt_3)$;

(3) compounds of the formula $R^7_n Al(OAlR^{10}_2)_{3-n}$, for example, $Et_2AlOAlEt_2$ and $(iso-Bu)_2AlOAl(iso-Bu)_2$;

(4) compounds of the formula $R^7_n Al(NR^{11}_2)_{3-n}$, for example, $Me_2AlNEt_2$, $Et_2AlNHMe$, $Me_2AlNHEt$, $Et_2AlN(SiMe_3)_2$ and $(iso-Bu)_2AlN(SiMe_3)_2$;

(5) compounds of the formula $R^7{}_n\text{Al}(SiR^{12}{}_3)_{3-n}$, for example, $(\text{iso-Bu})_2\text{AlSime}_3$; and (6) compounds of the formula $R^7{}_n\text{Al}(N(R^{13})\text{AlR}^{14}{}_2)_{3-n}$, for example, $\text{Et}_2\text{AlN(Me)AlEt}_2$ and $(\text{iso-Bu})_2\text{AlN(Et)Al(iso-Bu)}_2$.

Among the organoaluminum compounds represented by the formulas [III] and [IV], preferred are compounds of the formulas $R^7{}_3\text{Al}$, $R^7{}_n\text{Al}(OR^8)_{3-n}$ and $R^7{}_n\text{Al}(OAlR^{10}{}_2)_{3-n}$, and particularly preferred are compounds of those formulas wherein R is an isoalkyl group and n is 2.

In the present invention, in addition to the components (A), (B-1), (B-2) and (C), water may be used as a catalyst component. For example, there can be employed water dissolved in a polymerization solvent which will be described later, and adsorbed water or water of crystallization contained in compounds or salts used for preparing the component (B-1).

The first olefin polymerization catalyst according to the invention can be prepared by mixing the component (A) and the component (B-1) (or the component (B-2)), and if desired, water as a catalyst component, in an inert hydrocarbon solvent or an olefin solvent.

In this case, there is no specific limitation on the order of mixing each components, but it is preferred that the component (B-1) (or the component (B-2)) is mixed with water, followed by mixing with the component (A).

The second olefin polymerization catalyst according to the invention can be prepared by mixing the component (A), the component (B-1) (or the component (B-2)) and the component (C), and if desired, water as a catalyst component, in an inert hydrocarbon solvent or an olefin solvent.

In this case, there is also no specific limitation on the order of mixing each components. However, when the component (B-1) is used, it is preferred that the component (B-1) is mixed with the component (C), followed by mixing with the component (A). When the component (B-2) is used, it is preferred that the component (C) is mixed with the component (A), followed by mixing with the component (B-2).

In the mixing of each components, an atomic ratio (Al/transition metal) of aluminum in the component (B-1) to the transition metal in the component (A) is in the range of usually 10 to 10,000, preferably 20 to 5,000; and a concentration of the component (A) is in the range of about $10^{-8}$ to $10^{-1}$ mol/liter-solvent, preferably $10^{-7}$ to $5\times 10^{-2}$ mol/liter-solvent.

When the component (B-2) is used, a molar ratio (component (A) /component (B-2)) of the component (A) to the component (B-2) is in the range of usually 0.01 to 10, preferably 0.1 to 5; and a concentration of the component (A) is in the range of about $10^{-8}$ to $10^{-1}$ mol/liter-solvent, preferably $10^{-7}$ to $5\times 10^{-2}$ mol/liter-solvent.

In the second olefin polymerization catalyst of the invention, an atomic ratio $(\text{Al}_c/\text{Al}_{B-1})$ of the aluminum atom $(\text{Al}_c)$ in the component (C) to the aluminum atom $(\text{Al}_{B-1})$ in the component (B-1) is in the range of usually 0.02 to 20, preferably 0.2 to 10.

When water is used as a catalyst component, a molar ratio $(\text{Al}_{B-1}/\text{H}_2\text{O})$ of the aluminum atom $(\text{Al}_{B-1})$ in the component (B-1) to the water $(\text{H}_2\text{O})$ is in the range of 0.5 to 50, preferably 1 to 40.

Each of the above-mentioned components may be mixed in a polymerization reactor, or a mixture of those components previously prepared may be fed to a polymerization reactor.

If the components are previously mixed, the mixing temperature is in the range of usually $-50°$ to $150°$ C., preferably $-20°$ to $120°$ C., and the contact time is in the range of 1 to 1,000 minutes, preferably 5 to 600 minutes. The mixing temperature may be varied while the components are mixed and contacted with each other.

Examples of the inert hydrocarbon solvents for use in the preparation of the olefin polymerization catalysts of the invention include:

aliphatic hydrocarbons, such as propane, butane, pentane, hexane, heptane, octane, decane, dodecane and kerosine;

alicyclic hydrocarbons, such as cyclopentane, cyclohexane and methylcyclopentane;

aromatic hydrocarbons, such as benzene, toluene and xylene;

halogenated hydrocarbons, such as ethylene chloride, chlorobenzene and dichloromethane; and mixtures of the above hydrocarbons.

Next, the third and the fourth olefin polymerization catalysts according to the invention are explained.

The third olefin polymerization catalyst of the invention comprises:

a fine particle carrier;
(A) a transition metal compound represented by the above formula [I]; and
(B) at least one compound selected from the group consisting of (B-1) and (B-2) as defined above;
said transition metal compound (A) and said at least one compound (B) being supported on the fine particle carrier.

The fourth olefin polymerization catalyst of the invention is formed from:

a solid catalyst component which comprises:
a fine particle carrier,
(A) a transition metal compound represented by the above formula [I], and
(B) at least one compound selected from the group consisting of (B-1) and (B-2) as defined above;
said transition metal compound (A) and said at least one compound (B) being supported on the fine particle carrier; and
(C) an organoaluminum compound.

The transition metal compound (A) for use in the third and the fourth olefin polymerization catalysts of the invention is identical with the component (A) used for the aforesaid first and second olefin polymerization catalysts, and is a transition metal compound represented by the above formula [I].

Examples of the organoaluminum oxy-compounds (B-1) for use in the third and the fourth olefin polymerization catalysts of the invention are identical with those of the component (B-1) used for the aforesaid first and second olefin polymerization catalysts.

Examples of the compounds (B-2) which react with the transition metal compound (A) to form an ion pair and used for the third and the fourth olefin polymerization catalysts of the invention are identical with those of the component (B-2) used for the aforesaid first and second olefin polymerization catalysts.

Examples of the organoaluminum compounds (C) for use in the fourth olefin polymerization catalyst of the invention are identical with those of the component (C) used for the aforesaid second olefin polymerization catalyst.

The fine particle carrier used for the third and the fourth olefin polymerization catalysts of the invention is an inorganic or organic compound, and is a particulate or granular solid having a particle diameter of 10 to 300 μm, preferably 20 to 200 μm.

The inorganic carrier is preferably a porous oxide, and examples thereof include $SiO_2$, $Al_2O_3$, $MgO$, $ZrO_2$, $TiO_2$, $B_2O_3$, CaO, ZnO, BaO, $ThO_2$ and mixtures thereof such as $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Of these, preferred is a carrier containing $SiO_2$ and/or $Al_2O_3$.

The above-mentioned inorganic oxides may contain carbonates, sulfates, nitrates and oxides, e.g., $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$, in a small amount.

The properties of the fine particle carrier vary depending on the type and the process for the preparation thereof, but preferably used in the invention is a carrier having a specific surface area of 50 to 1,000 $m^2/g$, preferably 100 to 700 $m^2/g$, and a pore volume of 0.3 to 2.5 $cm^3/g$. The fine particle carrier may be used after calcined at a temperature of 100 to 1,000° C., preferably 50° to 700° C., if desired.

Also employable as the fine particle carrier in the invention is a granular or particulate solid of an organic compound having a particle diameter of 10 to 300 μm. Examples of such organic compounds include (co)polymers produced mainly from α-olefins of 2 to 14 carbon atoms such as ethylene, propylene, 1-butene and 4-methyl-1-pentene, and (co)polymers produced mainly from vinylcyclohexane or styrene.

The fine particle carrier may contain a surface hydroxyl group or water. In this case, the surface hydroxyl group is contained in an amount of not less than 1.0% by weight, preferably 1.5 to 4.0% by weight, more preferably 2.0 to 3.5% by weight; and water is contained in an amount of not less than 1.0% by weight, preferably 1.2 to 20% by weight, more preferably 1.4 to 15% by weight. The term "water contained in the fine particle carrier" means "water which is adsorbed on the surface of the fine particle carrier".

The amount (% by weight) of the adsorbed water and the amount (% by weight) of the surface hydroxyl group in the fine particle carrier can be determined in the following manner.

Amount of adsorbed water

The weight reduction of the fine particle carrier after drying at 200° C. under atmospheric pressure for 4 hours in a stream of nitrogen is taken as the amount of the adsorbed water.

Amount of surface hydroxyl group

The weight of the fine particle carrier after drying at 200° C. under atmospheric pressure for 4 hours in a stream of nitrogen is taken as X (g). The carrier is calcined at 1,000° C. for 20 hours to obtain a calcined product containing no surface hydroxyl group. The weight of the calcined product thus obtained is taken as Y (g). The amount of the surface hydroxyl group is calculated by the following equation:

Amount (wt. %) of surface hydroxyl group = $\{(X-Y)/X\} \times 100$

If a fine particle carrier containing the adsorbed water or the surface hydroxyl group in the specific amount is used, an olefin polymerization catalyst capable of producing an olefin polymer of excellent particle properties with high polymerization activity can be obtained.

In the third and the fourth olefin polymerization catalysts of the invention, such water as described for the first and the second olefin polymerization catalysts may be used as a catalyst component.

The third olefin polymerization catalyst of the invention (i.e., solid catalyst component) can be prepared by mixing the fine particle carrier, the component (A) and the component (B-1) (or the component (B-2)), and if desired, water, in an inert hydrocarbon solvent or an olefin medium. In the mixing of each components, the component (C) can be further added.

There is no specific limitation on the order of mixing these components.

However, preferred are:

a process in which the fine particle carrier is mixed and contacted with the component (B-1) (or the component (B-2)), and then with the component (A), followed by mixing with water if desired;

a process in which a mixture of the component (B-1) and (or the component (B-2)) and the component (A) is mixed and contacted with the fine particle carrier, followed by mixing with water if desired; and a process in which the fine particle carrier is mixed and contacted with the component (B-1) (or the component (B-2)) and water, followed by mixing with the component (A).

In the mixing of each components, the component (A) is used in an amount of usually $10^{-6}$ to $5 \times 10^{-3}$ mol, preferably $3 \times 10^{-6}$ to $10^{-3}$ mol, based on 1 g of the fine particle carrier; and a concentration of the component (A) is in the range of about $5 \times 10^{-6}$ to $2 \times 10^{-2}$ mol/liter-solvent, preferably $10^{-5}$ to $10^{-2}$ mol/liter-solvent. An atomic ratio (Al/transition metal) of aluminum in the component (B-1) to the transition metal in the component (A) is in the range of usually 10 to 3,000, preferably 20 to 2,000. When the component (B-2) is used, a molar ratio (component (A)/component (B-2)) of the component (A) to the component (B-2) is in the range of usually 0.01 to 10, preferably 0.1 to 5.

When water is used as a catalyst component, a molar ratio ($Al_{B-1}/H_2O$) of the aluminum atom ($Al_{B-1}$) in the component (B-1) to the water ($H_2O$) is in the range of 0.5 to 50, preferably 1 to 40.

In the mixing of each components, the temperature is in the range of usually −50° to 150° C., preferably −20° to 120° C.; and the contact time is in the range of 1 to 1,000 minutes, preferably 5 to 600 minutes. The mixing temperature may be varied while the components are mixed and contacted with each other.

The fourth olefin polymerization catalyst of the invention is formed from the above-mentioned third olefin polymerization catalyst (solid catalyst component) and the organoaluminum compound (C). The component (C) is used in an amount of not more than 500 mol, preferably 5 to 200 mol, based on 1 g·atom of the transition metal atom in the component (A).

Examples of the inert hydrocarbon media employable for preparing the third and the fourth olefin polymerization catalysts of the invention are identical with those used for the first and the second olefin polymerization catalysts.

Any of the previously discussed catalysts may be subjected to prepolymerization prior to use for the polymerization or copolymerization of an olefin; and such polymerization or copolymerization, subsequent to prepolymerization, may be carried out in the further presence of an organoaluminum compound.

Next, the fifth and the sixth olefin polymerization catalysts according to the invention are explained.

The fifth olefin polymerization catalyst of the invention is formed from:

a fine particle carrier;
(A) a transition metal compound represented by the above formula [I];
(B) at least one compound selected from the group consisting of (B-1) and (B-2) as defined above; and
an olefin polymer produced by prepolymerization.

The sixth olefin polymerization catalyst of the invention is formed from:

a fine particle carrier;

(A) a transition metal compound represented by the above formula [I];

(B) at least one compound selected from the group consisting of (B-1) and (B-2) as defined above;

(C) an organoaluminum compound; and an olefin polymer produced by prepolymerization.

Examples of the fine particle carrier for use in the fifth and the sixth olefin polymerization catalysts of the invention are identical with those used for the aforesaid third and fourth olefin polymerization catalysts.

The transition metal compound (A) for use in the fifth and the sixth olefin polymerization catalysts of the invention is identical with the component (A) used for the aforesaid first and second olefin polymerization catalysts, and is a transition metal compound represented by the above formula [I].

Examples of the organoaluminum oxy-compounds (B-1) for use in the fifth and the sixth olefin polymerization catalysts of the invention are identical with those of the component (B-1) used for the aforesaid first and second olefin polymerization catalysts.

Examples of the compounds (B-2) which react with the transition metal compound (A) to form an ion pair and used for the fifth and the sixth olefin polymerization catalysts of the invention are identical with those of the component (B-2) used for the aforesaid first and second olefin polymerization catalysts.

Examples of the organoaluminum compounds (C) for use in the sixth olefin polymerization catalyst of the invention are identical with those of the component (C) used for the aforesaid second olefin polymerization catalyst.

In the fifth and the sixth olefin polymerization catalysts of the invention, such water as described in the first and second olefin polymerization catalysts may be used as a catalyst component.

The fifth olefin polymerization catalyst of the invention can be prepared by prepolymerizing a small amount of an olefin in the presense of a solid catalyst component which is obtained by mixing the fine particle carrier, the component (A) and the component (B-1) (or the component (b-2)), and if desired, water, in an inert hydrocarbon medium. In the mixing of those components, the component (C) can be further added.

There is no specific limitation on the order of mixing each components.

However, preferred are:

a process in which the fine particle carrier is mixed and contacted with the component (B-1) (or the component (B-2)), and then with the component (A), followed by mixing with water if desired;

a process in which a mixture of the component (B-1) (or the component (B-2)) and the component (A) is mixed and contacted with the fine particle carrier, followed by mixing with water if desired; and a process in which the fine particle carrier is mixed and contacted with the component (B-1) (or the component (B-2)) and water, followed by mixing with the component (A).

The mixing of those components is desirably carried out with stirring.

In the mixing of each components, the component (A) is used in an amount of usually $10^{-6}$ to $5 \times 10^{-3}$ mol, preferably $3 \times 10^{-6}$ to $10^{-3}$ mol, based on 1 g of the fine particle carrier; and a concentration of the component (A) is in the range of about $5 \times 10^{-6}$ to $2 \times 10^{-2}$ mol/liter-solvent, preferably $10^{-5}$ to $10^{-2}$ mol/liter-solvent. An atomic ratio (Al/transition metal) of aluminum in the component (B-1) to the transition metal in the component (A) is in the range of usually 10 to 3,000, preferably 20 to 2,000. When the component (B-2) is used, a molar ratio (component (A)/component (B-2)) of the component (A) to the component (B-2) is in the range of usually 0.01 to 10, preferably 0.1 to 5.

When water is used as a catalyst component, a molar ratio ($Al_{B-1}/H_2O$) of the aluminum atom ($Al_{B-1}$) in the component (B-1) to the water ($H_2O$) iS in the range of 0.5 to 50, preferably 1 to 40.

In the mixing of the components, the temperature is in the range of usually $-50°$ to $150°$ C., preferably $-20°$ to $120°$ C.; and the contact time is in the range of 1 to 1,000 minutes, preferably 5 to 600 minutes. The mixing temperature may be varied while the components are mixed and contacted with each other.

The fifth olefin polymerization catalyst of the invention can be prepared by prepolymerizing an olefin in the presence of each of the above-mentioned components. The prepolymerization can be carried out by introducing an olefin into an inert hydrocarbon solvent in the presence of the above components and if necessary the component (C).

In the prepolymerization, the component (A) is used in an amount of usually $10^{-5}$ to $2 \times 10^{-2}$ mol/liter-solvent, preferably $5 \times 10^{-5}$ to $10^{-2}$ mol/liter-solvent. The prepolymerization temperature is in the range of $-20°$ to $80°$ C., preferably $0°$ to $50°$ C., and the prepolymerization time is in the range of 0.5 to 100 hours, preferably 1 to 50 hours.

The olefin for use in the prepolymerization is selected from olefins which are used for polymerization, and it is preferably the same monomer as used in the polymerization or a mixture of the same monomer as used in the polymerization and an α-olefin.

In the olefin polymerization catalyst of the invention obtained as above, the transition metal atom is desirably supported in an amount of about $10^{-6}$ to $10^{-3}$ g·atom, preferably $2 \times 10^{-6}$ to $3 \times 10^{-4}$ g·atom, based on 1 g of the fine particle carrier, and the aluminum atom is desirably supported in an amount of about $10^{-3}$ to $10^{-1}$ g·atom, preferably $2 \times 10^{-3}$ to $5 \times 10^{-2}$ g·atom, based on 1 g of the fine particle carrier. Further, the component (B-2) is desirably supported in an amount of $10^{-7}$ to 0.1 g·atom, preferably $2 \times 10^{-7}$ to $3 \times 10^{-2}$ g·atom, in terms of boron atom derived from the component (B-2).

The amount of the polymer produced through the prepolymerization is desired to be in the range of about 0.1 to 500 g, preferably 0.3 to 300 g, particularly preferably 1 to 100 g, based on 1 g of the fine particle carrier.

The sixth olefin polymerization catalyst of the invention is formed from the above-mentioned fifth olefin polymerization catalyst (component) and the organoaluminum compound (C). It is desired that the organoaluminum compound (C) is used in an amount of not more than 500 mol, preferably 5 to 200 mol, based on 1 g·atom of the transition metal atom in the component (A).

Examples of the inert hydrocarbon media employable for preparing the fifth and the sixth olefin polymerization catalysts of the invention are identical with those used for the first and the second olefin polymerization catalysts.

The first to the sixth olefin polymerization catalysts according to the invention may further contain other components than the components described above, which are useful for the olefin polymerization.

By the use of the olefin polymerization catalysts of the invention as described above, polyolefins having a high melting point and a high molecular weight can be obtained with high polymerization activity. Moreover, the thus obtained polyolefins have a narrow molecular weight distribution and a narrow composition distribution.

Next, the process for olefin polymerization according to the invention is described.

In the present invention, polymerization of an olefin is performed in the presence of any one of the above-mentioned olefin polymerization catalysts. The polymerization may be carried out by either a liquid phase polymerization process such as a suspension polymerization process, or a gas phase polymerization process.

In the liquid phase polymerization process, the same inert hydrocarbon solvent as used for the preparation of the above catalysts can be employed, or the olefin itself can be also employed as a solvent.

In the polymerization of an olefin using the first or the second olefin polymerization catalyst, the catalyst is used in an amount of usually $10^{-8}$ to $10^{-3}$ g·atom/liter, preferably $10^{-7}$ to $10^{-4}$ g·atom/liter, in terms of a concentration of the transition metal atom derived from the component (A) in the polymerization system.

In the polymerization of an olefin using the third or the fourth olefin polymerization catalyst, the catalyst is used in an amount of usually $10^{-8}$ to $10^{-3}$ g·atom/liter, preferably $10^{-7}$ to $10^{-4}$ g·atom/liter, in terms of a concentration of the transition metal atom derived from the component (A) in the polymerization system. In this case, an organoaluminum oxy-compound which is not supported on the carrier may be used, in addition to the organoaluminum oxy-compound (component (B-1)) supported on the carrier.

In the polymerization of an olefin using the olefin polymerization catalyst obtained by prepolymerizing an olefin, as in the fifth or the sixth olefin polymerization catalyst, the catalyst is used in an amount of usually $10^{-8}$ to $10^{-3}$ g·atom/liter, preferably $10^{-7}$ to $10^{-4}$ g·atom/liter, in terms of a concentration of the transition metal atom derived from the component (A) in the polymerization system. In this case, an organoaluminum oxy-compound which is not supported on the carrier may be used, in addition to the organoaluminum oxy-compound (component (B-1)) supported on the carrier.

In the slurry polymerization process, the temperature for the olefin polymerization is in the range of usually −50° to 100° C., preferably 0 to 90° C. In the liquid phase polymerization process, the temperature is in the range of usually 0° to 250° C., preferably 20° to 200° C. In the gas phase polymerization process, the temperature is in the range of 0° to 120° C., preferably 20° to 100° C. The polymerization pressure is in the range of usually atmospheric pressure to 100 kg/cm², preferably atmospheric pressure to 50 kg/cm². The polymerization reaction can be carried out either batchwise, semicontinuously or continuously. Further, the polymerization may be performed in two or more stages under different reaction conditions.

The molecular weight of the resulting olefin polymer can be regulated by the use of hydrogen in the polymerization system or by varying the polymerization temperature.

Examples of the olefins to be polymerized using the olefin polymerization catalysts of the invention include:

ethylene;

α-olefins of 3 to 20 carbon atoms, such as propylene, 1-butene, 1-pentene, 1-hexene, 4-methyl-1-pentene, 1-octene, 1-decene, 1-dodecene, 1-tetradecene, 1-hexadecene, 1-octadecene and 1-eicosene; and cycloolefins of 3 to 20 carbon atoms, such as cyclopentene, cycloheptene, norbornene, 5-methyl-2-norbornene, tetracyclododecene and 2-methyl-1,4,5,8-dimethano-1,2,3,4,4a,5,8,8a-octahydronaphthalene.

Also employable are styrene, vinylcyclohexane, diene, etc.

EFFECT OF THE INVENTION

The novel transition metal compound according to the invention can be used as an olefin polymerization catalyst component.

By the use of the olefin polymerization catalysts according to the invention, polyolefins having a high melting point, a high molecular weight, a narrow molecular weight distribution and a narrow composition distribution can be prepared with high polymerization activity.

The present invention is further described with reference to the following examples, but it should be construed that the invention is in no way limited to those examples.

In the present invention, an intrinsic viscosity [η], a molecular weight distribution (Mw/Mn) and a melting point (Tm) are determined as follows.

Intrinsic viscosity [η]

The intrinsic viscosity [η] was measured in decalin at 135° C., and expressed by dl/g.

Molecular weight distribution (Mw/Mn)

The molecular weight distribution (Mw/Mn) was measured in the following manner using GPC-150C produced by Milipore Co.

A separatory column of TSK-GNH-HT having a diameter of 72 mm and a length of 600 mm was used, and the column temperature was set to 140° C. A sample (concentration: 0.1% by weight, amount: 500 microliters) was moved in the column at a rate of 1.0 ml/min using o-dichlorobenzene (available from Wako Junyaku Kogyo K.K.) as a mobile phase and 0.025% by weight of BHT (Takeda Chemical Industries, Ltd.) as an antioxidant. A differential refractometer was used as a detector. With respect to standard polystyrenes, polystyrenes available from Toso Co., Ltd. were used as those of Mw<1,000 and Mw>4×10⁶, and polystyrenes available from Pressure Chemical Co. were used as those of 1,000<Mw<4×10⁶.

Melting point (Tm)

The melting point was sought from an endothermic curve given by heating about 5 mg of a sample charged in an aluminum pan to 200° C. at a rate of 10° C./rain, keeping it at 200° C. for 5 minutes, then cooling it to room temperature at a rate of 20° C./min and heating it at a rate of 10° C./min. The measurement was made using a DSC-7 type measuring device produced by Perkin Elmer Co.

Example 1

[Synthesis of rac-dimethylsilyl-bis(2-methyl-4-(p-trifluoromethylphenyl)-1-indenyl)zirconium dichloride]

The synthesis route is described below.

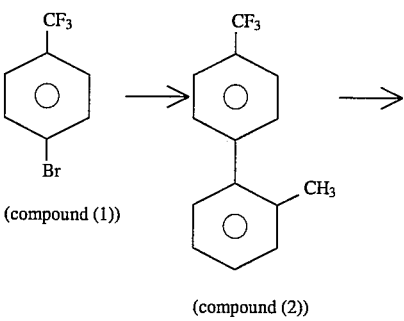

-continued (compound (3))

(compound (4))

(compound (5))

(compound (6))

(compound (7))

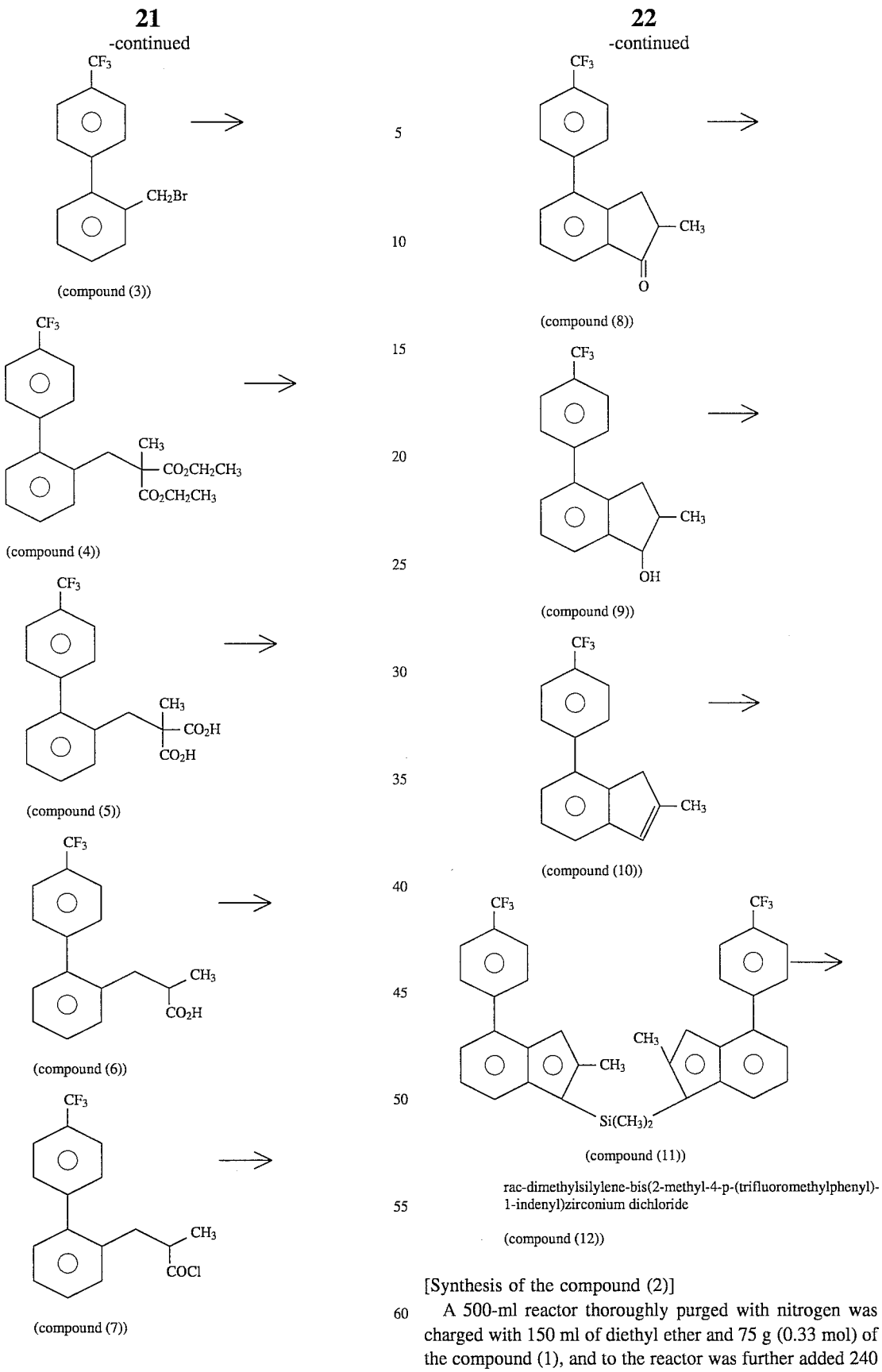

(compound (8))

(compound (9))

(compound (10))

(compound (11))

rac-dimethylsilylene-bis(2-methyl-4-p-(trifluoromethylphenyl)-1-indenyl)zirconium dichloride (compound (12))

[Synthesis of the compound (2)]

A 500-ml reactor thoroughly purged with nitrogen was charged with 150 ml of diethyl ether and 75 g (0.33 mol) of the compound (1), and to the reactor was further added 240 mg (0.33 mmol) of PdCl$_2$ (dppf). With stirring of the resulting mixture under ice cooling, 155 ml (0.33 mol) of a diethyl ether solution of a Grignard reagent prepared from o-bromotoluene and Mg was dropwise added to the mixture over a period of 30 minutes.

After the reaction was continued for 12 hours, the reaction solution was poured into a saturated ammonium chloride solution. Then, the ether phase was separated, washed with water and dried on anhydrous magnesium sulfate. Further, the ether was distilled off, and the residue was purified by means of silica gel chromatography (solvent: n-hexane). The resulting hexane solution was concentrated to obtain 71.0 g of an yellow oil (compound (2)) (yield: 92%, GC purity: 97%). The NMR of the obtained product (compound (2)) is set forth in Table 1. The NMR was measured in CDCl$_3$ at room temperature.

[Synthesis of the compound (3)]

A 1-liter four-necked flask was charged with 74.27 g (0.314 mol) of the compound (2), 58.74 g (0.330 mol) of N-bromosuccinimide and 500 ml of CCl$_4$. With stirring of the resulting mixture, 0.73 g (0.003 mol) of benzoyl peroxide was further added thereto, and the mixture was refluxed at a bath temperature of 85° C. for 5 hours.

After the mixture was allowed to stand for cooling, a powder produced was filtered by Kiriyama funnel. Then, the solvent was distilled off from the filtrate to obtain 103.35 g of an yellow-white powder (compound (3)) (yield: 100%, GC purity: 87%). The NMR of the obtained product (compound (3)) is set forth in Table 1.

[Synthesis of the compound (4)]

A 1-liter four-necked flask was charged with 39.16 g (0.349 tool) of potassium t-butoxide, 400 ml of toluene and 33.5 ml (0.349 mol) of N-methylpyrrolidone. With stirring of the resulting mixture under ice cooling, a solution obtained by dissolving 55.22 g (0.317 mol) of diethyl methylmalonate in 50 ml of toluene was dropwise added to the mixture over a period of 40 minutes (reaction temperature: 5° to 10° C.). After the addition was completed, the resulting mixture was stirred at 45° C. for 30 minutes, and further stirred at 65° C. for 1 hour. Then, a solution obtained by dissolving 100 g (0.317 mol) of the compound (3) in 50 ml of toluene was dropwise added over a period of 30 minutes under ice cooling (reaction temperature: 5° to 15° C.). The reaction mixture was stirred at room temperature for 30 minutes, and further stirred at 65° C. for 1.5 hours. Then, the reaction mixture was poured into 500 ml of water and adjusted to pH of about 1 using a 10% sulfuric acid.

Subsequently, the organic phase was separated, and the aqueous phase was extracted five times with 100 ml of toluene. The combined organic phases were washed four times with 200 ml of a saturated sodium chloride aqueous solution, and dried on MgSO$_4$. The solvent was distilled off to obtain 134.40 g of an yellow-brown liquid (compound (4)) (yield: 100%, GC purity: 90%).

[Synthesis of the compound (5)]

A 2-liter four-necked flask was charged with 134 g (0.331 mol) of the compound (4), 262 g (3.97 mol) of KOH (purity: 85%) and 1,000 ml of of 80% methanol, and the resulting mixture was refluxed for 4 hours. Then, the mixture was cooled in an ice bath to produce a white-yellow powder.

The powder was filtered by Kiriyama funnel, dissolved in 1 liter of water, and adjusted to pH of about 1 using a concentrated sulfuric acid to precipitate a powder, which was filtered by Kiriyama funnel and transferred into a 1 liter flask. To the powder in the flask was added 100 ml of ethanol, followed by treatment using an evaporator (azeotrope with H$_2$O). Finally, the resulting product was vacuum dried in a desiccator (on P$_2$O$_5$) to obtain a white-yellow powder (compound (5)) (yield: 72%). The NMR of the obtained product (compound (5)) is set forth in Table 1.

[Synthesis of the compound (6)]

A 1-liter flask was charged with 80 g (0.227 mol) of the compound (5), and the flask was placed in an oil bath of 80° C. Immediately, a gas (CO$_2$) generates, and the powder turns into liquid. After 2 hours, the liquid was cooled in a water bath, and 300 ml of CH$_2$Cl$_2$ was added thereto, followed by sufficient stirring. Then, insoluble substances were removed by the use of Kiriyama funnel. The solvent was removed from the filtrate to obtain 63.3 g of an yellow-white semi-solid (compound (6)) (yield: 90%). The NMR of the obtained product (compound (6)) is set forth in Table 1.

[Synthesis of the compound (7)]

A 500-ml flask was charged with 63.3 g (0.205 mol) of the compound (6) and 150 ml of SOCl$_2$, and the resulting mixture was refluxed for 2 hours.

After SOCl$_2$ was distilled off by means of single distillation, vacuum distillation was performed to obtain 48.0 g of a light yellow-green transparent liquid (compound (7)) (boiling point: 150° to 155° C./1 mmHg, yield: 72%). The NMR of the obtained product (compound (7)) is set forth in Table 1.

[Synthesis of the compound (8)]

A 1-liter four-necked flask was charged with 42 g (0.129 mol) of the compound (7) and 500 ml of CH$_2$Cl$_2$, and 23 ml (0.258 mol) of trifluoromethanesulfonic acid was dropwise added thereto at −78° C. over a period of 30 minutes. After the addition was completed, the temperature of the system was elevated to room temperature, and the resulting mixture was stirred for 1 hour. Then, the mixture was poured into a saturated NaHCO$_3$ aqueous solution, extracted four times with 200 ml of CH$_2$Cl$_2$, then washed three times with 200 ml of a saturated sodium chloride aqueous solution, and dried on MgSO$_4$. The solvent was distilled off to obtain 42 g of an yellow-white powder, which was subjected to column separation (SiO$_2$, Hexane-ethyl acetate) to obtain 33.72 g of a white powder (compound (8)) (yield: 90%). The NPrR of the obtained product (compound (8)) is set forth in Table 1.

[Synthesis of the compound (9)]

A 1-liter four-necked flask was charged with 31.5 g (0.109 mol) of the compound (8) and 500 ml of ethanol. With stirring of the resulting mixture under ice cooling, 2.06 g of NaBH$_4$ was added to the mixture over a period of 30 minutes by means of a spatula.

After stirring for 3 hours at room temperature, the reaction solution was poured into 150 ml of ice water, and ethanol was distilled off using a rotary evaporator. The residue was transferred into a separatory funnel, and extracted with 200 ml of ether. The aqueous phase was extracted three times with 100 ml of ether, and the combined ether phases were dried on MgSO$_4$. The solvent was distilled off to obtain 30.89 g of a light yellow-white powder (compound (9)) (yield: 97%). The NMR of the obtained product (compound (9)) is set forth in Table 1.

[Synthesis of the compound (10)]

A 1-liter eggplant-type flask was charged with 25.56 g (0.087 mol) of the compound (9), 8.37 g of paratoluenesulfonic acid monohydrate and 750 ml of benzene, and the mixture was refluxed for 1 hour by means of a Dienstark condenser. After cooling, the reaction solution was transferred into a 1-liter separatory funnel, washed five times with 200 ml of a saturated NaHCO$_3$ aqueous solution, and dried on MgSO$_4$. The solvent was distilled off to obtain 24 g of an yellow-white powder, which was subjected to column purification (SiO$_2$, hexane) to obtain 23.32 g of a white-yellow powder (compound (10) (yield: 98 The NMR of the obtained product (compound (10)) is set forth in Table 1.

[Synthesis of the compound (11)]

A 300-ml four-necked flask was charged with 8 g (29.2 mmol) of the compound (10) and 73 mg of CuCN and 70 ml of ether, and 18 ml of n-butyllithium (1.63 mmol/ml-solution) was dropwise added to the mixture over a period of 20 minutes at −10° C. with stirring. Then, the temperature of the resulting mixture was elevated to room temperature, followed by stirring for 30 minutes at 40° C. Thereafter, the mixture was again cooled to −10° C., and 1.77 ml of Me$_2$SiCl$_2$ was added thereto over a period of 10 minutes. After stirring at room temperature for 2 hours, the reaction solution was poured into a saturated ammonium chloride solution, extracted five times with 100 ml of ether, and dried on MgSO$_4$. After the solvent was distilled off, the residue was subjected to column purification to obtain 7.74 g of a white-yellow powder (compound (11)) (yield: 88%). The NMR of the obtained product (compound (11)) is set forth in Table 1.

[Synthesis of rac-dimethylsilylene-bis(2-methyl-4-(p-trifluoromethylphenylindenyl)zirconium dichloride (compound (12))]

A 200-ml three-necked reactor (equipped with a stirrer tip, a condenser, a dropping funnel and a thermometer) was charged with 5.10 g (8.44 mmol) of dimethylsilyl-bis(2-methyl-4-p-trifluoromethylphenylindene) (compound (11)) and 100 ml of anhydrous ether in an argon atmosphere, and 10.40 ml (16.9 mmol) of a hexane solution of n-butyllithium having a concentration of 1.63M was dropwise added thereto slowly at room temperature. After the addition was completed, the resulting mixture was further reacted for 13.5 hours. The reaction solution was cooled to −70° C. in a dry ice-acetone bath, and 1.97 g (8.44 mmol) of a ZrCl$_4$ powder was gradually added thereto. After the addition was completed, the solution was stirred overnight. Then, the solvent was distilled off at room temperature under reduced pressure. To the residue was added 100 ml of methylene chloride, then insoluble substances were filtered off, and the filtrate was concentrated at room temperature to precipitate a solid, which was filtered and then vacuum dried to obtain 0.17 g of an yellow solid (yield: 4%).

The product thus obtained was subjected to FD mass spectrometry, with the result of 762 (M$^+$).

The NMR of the obtained product (compound (12)) is set forth in Table 1.

TABLE 1

| Compound No. | $^1$H NMR spectrum (ppm) |
| --- | --- |
| (2) | 2.32(3H, s), 7.2–8.0(8H, m) |
| (3) | 4.45(2H, s), 7.1–8.0(8H, m) |
| (5) | 1.73(3H, s), 3.92(2H, s), 7.7–8.6(8H, m) |
| (6) | 0.88(3H, d, J=6.4Hz), 2.1–3.2(3H, m), 6.8–7.8(8H, m) |
| (7) | 1.10(3H, d, J=6.4Hz), 2.5–3.4(3H, m), 7.0–7.9(8H, m) |
| (8) | 1.32(3H, d, J=7.2Hz), 7.5–3.0(2H, m), 3.2–3.7(1H, m), 7.4–8.2(7H, m) |
| (9) | 1.15, 1.25(3H, d, J=7.2Hz), 1.5–1.9(1H, br), 2.0–3.3(3H, m), 4.85, 5.12(1H, d, J=7.2Hz), 7.2–8.0(7H, m) |
| (10) | 2.20(3H, s), 3.40(2H, s), 6.65(1H, s), 7.1–7.9(7H, m) |
| (11) | −0.20—−0.11(6H, m), 2.1–2.4(6H, m), 3.84(2H, s), 6.85(2H, s), 7.2–8.0(14H, m) |

TABLE 1-continued

| Compound No. | $^1$H NMR spectrum (ppm) |
| --- | --- |
| (12) | 1.30(6H, s), 2.19(6H, s), 6.82(2H, s), 7.08(2H, dd, J=7.0Hz), 7.33(2H, d, J=7.0Hz), 7.60–7.70(10H, m) |

Example 2

A 500-ml glass polymerization reactor thoroughly purged with nitrogen was charged with 400 ml of dried toluene. The temperature was elevated to 45° C., and to the reactor were added 0.2 mmol of triisobutylaluminum, 0.2 mmol of methylaluminoxane and 0.001 mmol (in terms of Zr atom) of rac-dimethylsilylene-bis(2-methyl-4-(p-trifluoromethylphenyl)-1-indenyl)zirconium dichloride while introducing propylene, to perform polymerization at 50° C. for 1 hour. After the polymerization, propylene was removed by deaeration, and the resulting polymer was dried at 80° C. for 10 hours.

The amount of the polymer thus obtained was 73 g, and the polymerization activity was 73 kgPP/mmol-Zr. This polymer had [η] of 2.40 dl/g, Mw/Mn of 2.4 and a melting point of 157.1° C.

Comparative Example 1

The procedure of Example 2 was repeated except that rac-dimethylsilylene-bis(2-methyl-4-isopropylindenyl)zirconium dichloride was used in place of rac-dimethylsilylene-bis(2-methyl-4-(p-trifluoromethylphenyl)-1-indenyl)zirconium dichloride, to polymerize propylene.

The amount of the polymer obtained was 47 g, and the polymerization activity was 47 kgPP/mmol-Zr. This polymer had [η] of 1.88 dl/g, Mw/Mn of 2.1 and a melting point of 148.7° C.

Comparative Example 2

The procedure of Example 2 was repeated except that rac-dimethylsilylene-bis(2-methyl-4-phenylindenyl)zirconium dichloride was used in place of rac-dimethylsilylene-bis(2-methyl-4-(p-trifluoromethylphenyl)-1-indenyl)zirconium dichloride, to polymerize propylene.

The amount of the polymer obtained was 59 g, and the polymerization activity was 59 kgPP/mmol-Zr. This polymer had [η] of 1.56 dl/g, Mw/Mn of 2.0 and a melting point of 155.8° C.

Example 3

A 500-ml glass polymerization reactor thoroughly purged with nitrogen was charged with 400 ml of dried toluene. The temperature was elevated to 45° C., and to the reactor were added 0.2 mmol of triethylaluminum, 0.001 mmol (in terms of Zr atom) of rac-dimethylsilylene-bis(2-methyl-4-(p-fluoromethylphenyl)-1-indenyl)zirconium dichloride and 0.002 mmol (in terms of B atom) of tris (pentafluorophenyl) boron while introducing propylene, to perform polymerization at 50° C. for 1 hour. After the polymerization, propylene was removed by aleaeration, and the resulting polymer was dried at 80° C. for 10 hours.

The amount of the polymer thus obtained was 70 g, and the polymerization activity was 70 kgPP/mmol-Zr. This polymer had [η] of 2.4 dl/g, Mw/Mn of 2.2 and a melting point of 157.1° C.

What is claimed is:

1. A process for olefin polymerization comprising polymerizing or copolymerizing an olefin in the presence of an olefin polymerization catalyst from the group consisting of:

(1) an olefin polymerization catalyst comprising (A) a transition metal compound represented by the following formula (I)

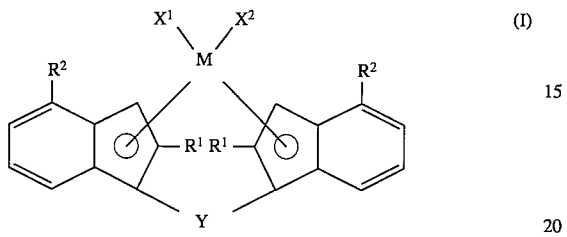

wherein M is a transition metal of Group IVa, Va or VIa of the periodic table, each $R^1$ is a hydrocarbon group of 1 to 20 carbon atoms, each $R^2$ is an aryl group of 6 to 16 carbon atoms substituted with a halogenated methyl group, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$— where R$^3$ is a hydrogen atom, a halogen atom, a hydrocarbon group of 1 to 20 carbon atoms or a halogenated hydrocarbon group of 1 to 20 carbon atoms, and (B) at least one compound selected from the group consisting of (B-1) an aluminoxane, and (B-2) a compound which reacts with the transition metal compound (A) to form an ion pair;

(2) an olefin polymerization catalyst comprising (A) a transition metal compound represented by the following formula (I)

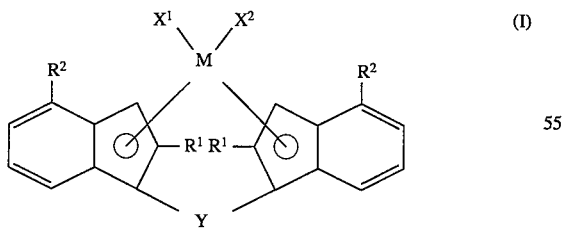

wherein M is a transition metal of Group IVa, Va or VIa of the periodic table, each $R^2$ is a hydrocarbon group of 1 to 20 carbon atoms, each $R^2$ is an aryl group of 6 to 16 carbon atoms substituted with a halogenated methyl group, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and Y is a divalent hydrocarbon group of 1 to 20 carbon atoms, a divalent halogenated hydrocarbon group of 1 to 20 carbon atoms, a divalent silicon-containing group, a divelent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$— where R$^3$ is a hydrogen atom, a halogen atom, a hydrocarbon group of 1 to 20 carbon atoms or a halogenated hydrocarbon group of 1 to 20 carbon atoms, (B) at least one compound selected from the group consisting of (B-1) an aluminoxane, and (B-2) a compound which reacts with the transition metal compound (A) to form an ion pair, and (C) an organoaluminum compound represented by the following formula (III)

$$R^7{}_n Al\, X_{3-n} \qquad (III)$$

wherein $R^7$ is a hydrocarbon group of 1 to 12 carbon atoms, X is a halogen atom or a hydrogen atom and n is 1 to 3;

(3) an olefin polymerization catalyst comprising (A) a transition metal compound represented by the following formula (I)

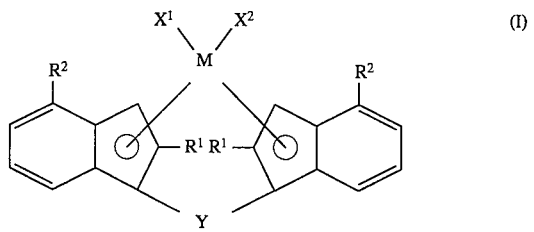

wherein M is a transition metal of Group IVa, Va or VIa of the periodic table, each $R^1$ is a hydrocarbon group of 1 to 20 carbon atoms, each $R^2$ is an aryl group of 6 to 16 carbon atoms substituted with a halogenated methyl group, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$— where R$^3$ is a hydrogen atom, a halogen atom, a hydrocarbon group of 1 to 20 carbon atoms or a halogenated hydrocarbon group of 1 to 20 carbon atoms, (B) at least one compound selected from the group consisting of (B-1) an aluminoxane, and (B-2) a compound which reacts with the transition metal compound (A) to form an ion pair, and a fine particle carrier, wherein said transition metal compound (A) and said at least one compound (B) are supported on the fine particle carrier;

(4) an olefin polymerization catalyst comprising
(A) a transition metal compound represented by the following formula (I)

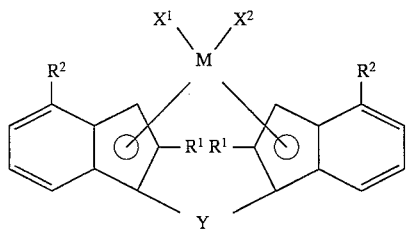

wherein M is a transition metal of Group IVa, Va or VIa of the periodic table,
each $R^1$ is a hydrocarbon group of 1 to 20 carbon atoms,
each $R^2$ is an aryl group of 6 to 16 carbon atoms substituted with a halogenated methyl group,
$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and
Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$— where $R^3$ is a hydrogen atom, a halogen atom, a hydrocarbon group of 1 to 20 carbon atoms or a halogenated hydrocarbon group of 1 to 20 carbon atoms,
(B) at least one compound selected from the group consisting of
(B-1) an aluminoxane, and
(B-2) a compound which reacts with the transition metal compound (A) to form an ion pair,
(C) an organoaluminum compound represented by the following formula (III)

 (III)

wherein $R^7$ is a hydrocarbon group of 1 to 12 carbon atoms, X is a halogen atom or a hydrogen atom and n is 1 to 3, and
a fine particle carrier, wherein said transition metal compound (A), said at least one compound (B) and said organoaluminum compound (C) are supported on the fine particle carrier;

(5) an olefin polymerization catalyst comprising
(i) a solid catalyst component comprising
(A) a transition metal compound represented by the following formula (I)

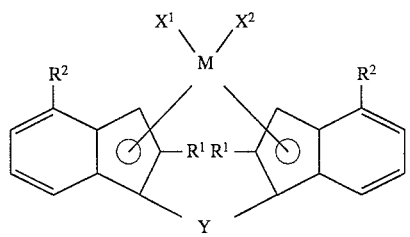

wherein M is a transition metal of Group IVa, Va or VIa of the periodic table,
each $R^1$ is a hydrocarbon group of 1 to 20 carbon atoms,
each $R^2$ is an aryl group of 6 to 16 carbon atoms substituted with a halogenated methyl group,
$X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and
Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR— where $R^3$ is a hydrogen atom, a halogen atom, a hydrocarbon group of 1 to 20 carbon atoms or a halogenated hydrocarbon group of 1 to 20 carbon atoms,
(B) at least one compound selected from the group consisting of
(B-1) an aluminoxane, and
(B-2) a compound which reacts with the transition metal compound (A) to form an ion pair, and a fine particle carrier,
wherein said transition metal compound (A) and said at least one compound (B) are supported on the fine particle carrier, and
(ii) an organoaluminum compound represented by the following formula (III)

 (III)

wherein $R^7$ is a hydrocarbon group of 1 to 2 carbon atoms, X is a halogen atom or a hydrogen atom and n is 1 to 3; and (6) an olefin polymerization catalyst comprising
(i) a solid catalyst component comprising
(A) a transition metal compound represented by the following formula (I)

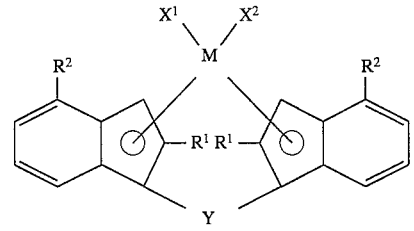

wherein M is a transition metal of Group IVa, Va or VIa of the periodic table,
each $R^1$ is a hydrocarbon group of 1 to 20 carbon atoms, each $R^2$ is an aryl group of 6 to 16 carbon atoms substituted with a halogenated methyl group, $X^1$ and $X^2$ are each a hydrogen atom, a halogen atom, a hydrocarbon group of 1 to 20 carbon atoms, a halogenated hydrocarbon group of 1 to 20 carbon atoms, an oxygen-containing group or a sulfur-containing group, and Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^3$—, —P(R$^3$)—, —P(O)(R$^3$)—, —BR$^3$— or —AlR$^3$— where $R^3$ is a hydrogen atom, a halogen atom, a hydrocarbon group of 1 to 20 carbon atoms or a halogenated hydrocarbon group of 1 to 20 carbon atoms, (B) at least one compound selected from the group consisting of (B-1) an aluminoxane, and (B-2) a compound which reacts with the transition metal compound (A) to form an ion pair, (C) an organoaluminum compound represented by the following formula (III)

$$R^7{}_n Al\, X_{3-n} \qquad (III)$$

wherein $R^7$ is a hydrocarbon group of 1 to 12 carbon atoms, X is a halogen atom or a hydrogen atom and n is 1 to 3, and a fine particle carrier, wherein said metal compound (A), said at least one compound (B) and said organoaluminum compound (C) are supported on the fine particle carrier, and (ii) an organoaluminum compound represented by the following formula (III)

$$R^7{}_n Al\, X_{3-n} \qquad (III)$$

wherein $R^7$ is a hydrocarbon group of 1 to 12 carbon atoms, X is a halogen atom or a hydrogen atom and n is 1 to 3.

2. The process as claimed in claim 1, wherein said olefin polymerization catalyst (1) further comprises an olefin polymer produced by prepolymerization of an olefin with said olefin polymerization catalyst (1) as defined in claim 1.

3. The process as claimed in claim 1, wherein said olefin polymerization catalyst (2) further comprises an olefin polymer produced by prepolymerization of an olefin with said olefin polymerization catalyst (2) as defined in claim 1.

4. The process as claimed in claim 1, wherein said olefin polymerization catalyst (3) further comprises an olefin polymer produced by prepolymerization of an olefin with said olefin polymerization catalyst (3) as defined in claim 1.

5. The process as claimed in claim 1, wherein said olefin polymerization catalyst (4) further comprises an olefin polymer produced by prepolymerization of an olefin with said olefin polymerization catalyst (4) as defined in claim 1.

6. The process as claimed in claim 1, wherein said olefin polymerization catalyst (5) further comprises an olefin polymer produced by prepolymerization of an olefin with said olefin polymerization catalyst (5) as defined in claim 1.

7. The process as claimed in claim 1, wherein said olefin polymerization catalyst (6) further comprises an olefin polymer produced by prepolymerization of an olefin with said olefin polymerization catalyst (6) as defined in claim 1.

8. The process as claimed in claim 1, wherein said transition metal compound (A) contains titanium, zirconium or hafnium as the transition metal.

9. The process as claimed in claim 8 wherein said transition metal is zirconium.

10. The process as claimed in claim 1, wherein in said transition metal compound (A) in said moiety $R^2$ said halogenated methyl group is a trifluoromethyl group.

11. The process as claimed in claim 10, wherein $R^2$ is selected from the group consisting of o-trifluoromethylphenyl, m-trifluoromethylphenyl, p-trifluoromethylphenyl, 2,4-di-trifluoromethylphenyl and 3,5-di-trifluoromethylphenyl.

12. The process as claimed in claim 1, wherein in said transition metal compound (A) said moieties $X^1$ and $X^2$ are selected from the group consisting of halogen atoms and hydrocarbon groups of 1 to 20 carbon atoms.

13. The process as claimed in claim 1, wherein in said transition metal compound (A) said moiety Y is selected from the group consisting of divalent silicon-containing groups, divalent germanium-containing groups and divalent tin-containing groups.

14. The process as claimed in claim 13, wherein said moiety Y is a divalent silicon-containing group selected from the group consisting of alkylsilylene, alkylarylsilylene and arylsilylene.

15. The process as claimed in any of claims 2–7 wherein said prepolymerization is conducted at a temperature in the range of –20° to 80° C. for a time of 0.5 to 100 hours.

16. The process as claimed in claim 1, wherein said olefin is selected from the group consisting of ethylene, α-olefins of 3 to 20 carbon atoms and cycloolefins of 3 to 20 carbon atoms.

17. The process as claimed in claim 2, wherein an organoaluminum compound as added to said prepolymerized catalyst.

18. The process as claimed in claim 3, wherein an organoaluminum compound is added to said prepolymerized catalyst.

19. The process as claimed in claim 4, wherein an organoaluminum compound is added to said prepolymerized catalyst.

20. The process as claimed in claim 5, wherein an organoaluminum compound is added to said prepolymerized catalyst.

21. The process as claimed in claim 6, wherein an organoaluminum compound is added to said prepolymerized catalyst.

22. The process as claimed in claim 7, wherein an organoaluminum compound as added to said prepolymerized catalyst.

* * * * *

UNITED STATES PATENT AND TRADEMARK OFFICE
Certificate

Patent No. 5,616,663                                                      Patented: April 1, 1997

On petition requesting issuance of a certificate for correction of inventorship pursuant to 35 U. S. C. 256, it has been found that the above-identified patent, through error and without deceptive intent, improperly sets forth the inventorship.

Accordingly, it is hereby certified that the correct inventorship of this patent is: Junichi Imuta, Waki-cho, Japan; Junji Saito, Waki-cho, Japan; and Takashi Ueda, Waki-cho, Japan.

Signed and Sealed this Fourteenth Day of April, 1998.

*JOSEPH L. SCHOFER*
*Supervisory Patent Examiner*
*Art Unit 1713*

UNITED STATES PATENT AND TRADEMARK OFFICE
CERTIFICATE OF CORRECTION

PATENT NO. : 5,616,663
DATED : April 1, 1997
INVENTOR(S) : JUNICHI IMUTA, ET AL.

It is certified that error appears in the above-indentified patent and that said Letters Patent is hereby corrected as shown below:

In Claim 1, column 27, line 8, between "catalyst" and "from", insert --selected--.

Signed and Sealed this

Second Day of June, 1998

Attest:

BRUCE LEHMAN

*Attesting Officer*   *Commissioner of Patents and Trademarks*